(12) United States Patent
Choi et al.

(10) Patent No.: US 7,622,305 B2
(45) Date of Patent: Nov. 24, 2009

(54) MULTIPLE ACID SOLUTION CHARACTERIZATION

(75) Inventors: Hok-Kin Choi, San Jose, CA (US); Vani Thirumala, San Jose, CA (US); Yongmei Wu, San Jose, CA (US)

(73) Assignee: Intel Corporation, Santa Clara, CA (US)

( * ) Notice: Subject to any disclaimer, the term of this patent is extended or adjusted under 35 U.S.C. 154(b) by 442 days.

(21) Appl. No.: 11/509,981

(22) Filed: Aug. 25, 2006

(65) Prior Publication Data

US 2008/0063564 A1   Mar. 13, 2008

(51) Int. Cl.
*G01N 33/53* (2006.01)
*G01N 37/00* (2006.01)

(52) U.S. Cl. .................. 436/163; 422/68.1; 436/51; 436/84

(58) Field of Classification Search .................. 436/163
See application file for complete search history.

(56) References Cited

U.S. PATENT DOCUMENTS 5,569,443 A * 10/1996 Wilson et al. ............ 423/576.6

OTHER PUBLICATIONS

Jeitziner, M.. Complexometric titration reagents, Sigma. Issue 3, 2004.*
Bultov, M.I. Titrimetric Determination of Acids in the Presence of Metal Ions., Zhurnal of Analiticheskoy Khimii, 38:9, pp. 1607-1610, 1983.*
Bulatov, M.I. Titrimetric Determination of Acids in the Presence of Metal Ions., Zhurnal of Analiticheskoy Khimii, 38:9, pp. 1607-1610, 1983.*

* cited by examiner

*Primary Examiner*—Krishnan S Menon
*Assistant Examiner*—Rebecca Fritchman
(74) *Attorney, Agent, or Firm*—Lee & Hayes, PLLC (57) ABSTRACT

Embodiments of techniques for determining the concentrations of one or more acid components of a multiple acid solution are presented herein.

23 Claims, 4 Drawing Sheets

MULTIPLE ACID SOLUTION CHARACTERIZATION

BACKGROUND

Acid solutions including multiple acids may be used in a variety of processes in industry, manufacturing, research, quality control and so forth. These acids may also be used for a variety of purposes such as for buffer solutions, catalysts, complexing agents, and so forth. However, accurate determination of the concentrations of the acid components of the multiple acid solutions may be hindered by effects of the multiple acids in the solution and the interaction of theses acids.

BRIEF DESCRIPTION OF THE DRAWINGS

The same reference numbers are utilized in instances in the discussion to reference like structures and components.

DETAILED DESCRIPTION

In the following discussion, exemplary techniques are described which may be employed to determine the concentration of components of a multiple acid solution. In a solution containing a weak acid, a strong acid, and an aminopolycarboxylic acid, determination of the concentrations of the individual acids in the solution by titration may be hindered because the aminopolycarboxylic acid may cause interference with the titration. In particular, the aminopolycarboxylic may act as both a strong and weak acid and thus titration of the associated solution may not produce discernable endpoints. The described techniques may be employed to reduce or remove the interference from aminopolycarboxylic acid with titration. More particularly, in accordance with one or more embodiments, the interference typically caused by the aminopolycarboxylic acid may be reduced and/or substantially removed such that the concentrations of the weak acid and the strong acid in the solution may be determined using titration.

Figure 1:
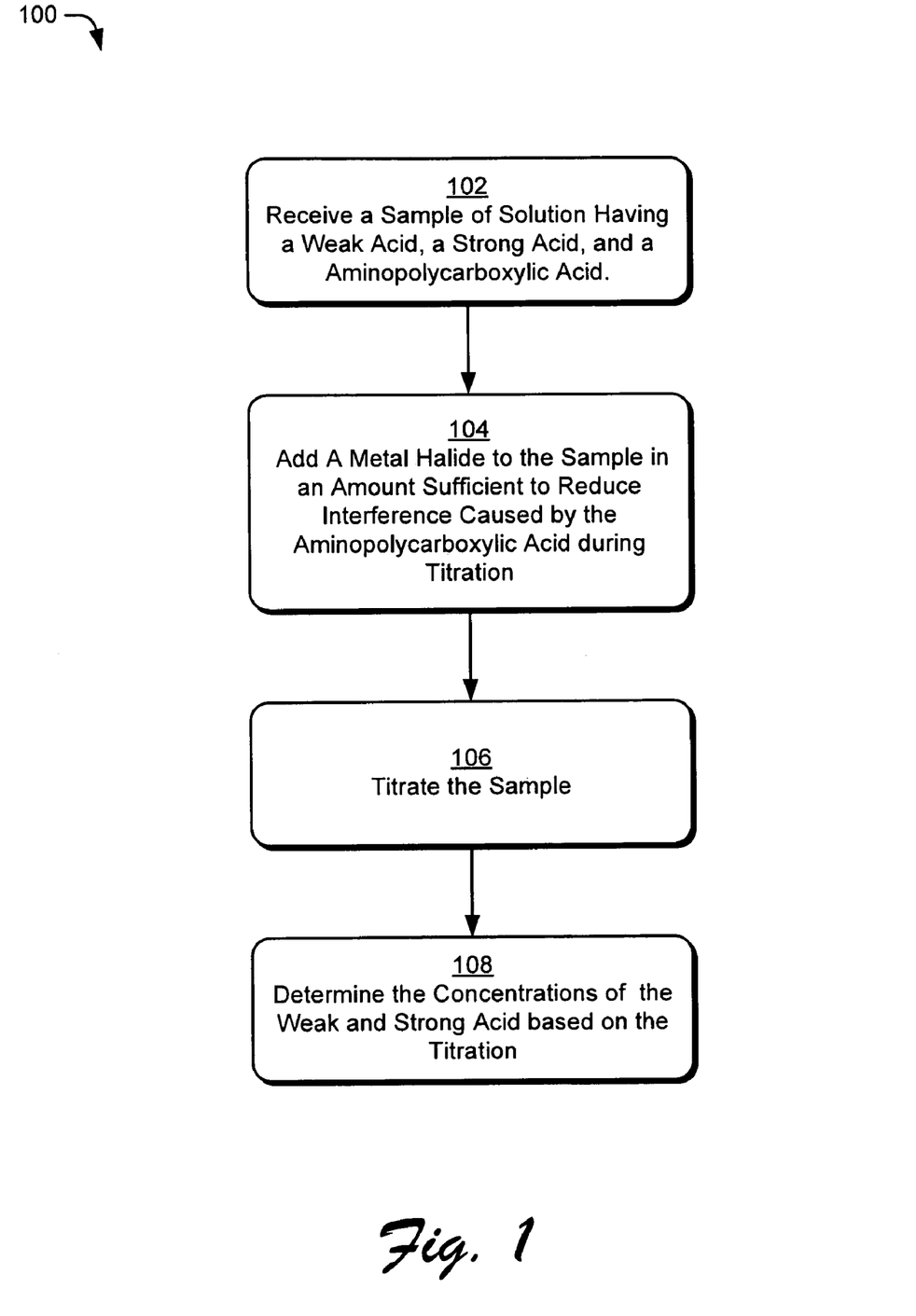
FIG. 1 is flow diagram depicting a procedure in an exemplary implementation in which the concentrations of components in a multiple acid solution are determined.

FIG. 1 depicts a flow diagram of an exemplary procedure 100 which may be employed to determine the concentrations of components in a multiple acid solution. The procedure is shown as a set of blocks that specify operations performed by one or more devices and/or technicians and are not necessarily limited to the orders shown for performing the operations by the respective blocks.

A sample is received of solution having a weak acid, a strong acid, and an aminopolycarboxylic acid (block 102). For instance, the composition and/or concentrations of a solution which includes at least a weak acid, a strong acid, and an aminopolycarboxylic acid may be sought for a variety of reasons, such as to ensure quality of a batch of the solution, to control process conditions, to maintain quality of products produced using the solution, and the like. Thus, a sample of the solution may be obtained by a technician, a sampling device, a probe and so forth, such that the sample may be tested to determine the composition and/or concentrations of the solution.

A metal halide compound is added to the sample in amount sufficient to reduce interference caused by the aminopolycarboxylic acid during titration (block 104). It accordance with the principles described herein, one or more metal halide compounds may be added to a solution which includes a weak acid, a strong acid, and an aminopolycarboxylic acid in order to reduce and/or substantially remove the interference typically caused by the aminopolycarboxylic acid in a titration of the solution. In an implementation metal halide compounds of transition metals from group 10 of the periodic table of elements are employed, further discussion of which may be found in relation to FIG. 2. Without wishing to be bound by theory it is believed that a stable complex is formed between the metal in the halide compound and the aminopolycarboxylic acid. The formation of the complex results in the carboxyl groups of the aminopolycarboxylic acid being liganded to the metal of the metal halide. Thus, the carboxyl groups are "tied up" such that the complexed aminopolycarboxylic acid will no longer interfere (e.g., interference is substantially removed) with titration of the solution.

The sample is titrated (block 106). For instance, the sample having the metal halide-aminopolycarboxylic acid complex may be titrated. Those skilled in the art will understand standard titration techniques which may be used to determine the concentrations of the components in a solution. Titration may occur via an automatic titration device, manual laboratory techniques, and so forth. Titration typically measures the change in pH of a sample as a known titrant is added to the sample. For instance, a base such as sodium hydroxide (NaOH), in a known concentration may be used as the titrant for the multiple acid solutions described herein. When titration is complete, a plot or analysis of the pH of the titrated solution versus the amount of titrant added may be used to determine endpoints of the titration which correspond to the amounts of strong and weak acid.

Then, concentrations of the weak and strong acid are determined based on the titration (block 108). For instance, based upon the endpoints determined from the titration, standard titration calculations may be employed to determine the concentrations of the weak and strong acid respectively, further discussion of which may be found in relation to FIG. 2.

The described solution including at least a weak acid, a strong acid, and an aminopolycarboxylic acid may be produced for a variety of purposes in industry, in manufacturing, in research and so on. For instance, such a solution may be employed as a buffer, a chelating agent, a complexing agent, a catalyst and so forth. In an implementation, the solution is configured for a catalyst bath to catalyze an electroless plating operation performed during the manufacture of integrated circuits, further discussion of which may be found in relation to FIGS. 3 and 4. Although certain embodiments are described in reference to a catalyst bath for an electroless plating operation, this is but one illustrative example and it is contemplated that the described techniques may be applied to determine the composition and/or concentrations of solutions used for many purposes inside and outside of integrated circuit manufacturing.

A variety of weak acids are contemplated including but not limited to acetic acid, citric acid, boric acid, formic acid and so forth. As those skilled in the art will appreciate weak acids are these which typically do not fully dissociate (less than 100% dissociated in aqueous solution) and may have dissociation constants (Ka) of between about $1.8 \times 10^6$ and 55.5. Conventionally, weak acids may be represented by the general formula HA.

As those skilled in the art will appreciate strong acids are these which typically fully dissociate (near 100% dissociation in aqueous solution) and may have dissociation constants (Ka) of about 55.5 or greater. A variety of strong acids are also contemplated including but not limited to hydrochloric acid (HCL), hydrobromic acid (HBr), hydroiodic acid (HI), sulfuric acid ($H_2SO_4$), nitric acid ($HNO_3$), perchloric acid ($HClO_4$), chloric acid ($HClO_3$), and so forth.

A variety of aminopolycarboxylic acids are contemplated including but not limited to ethylenediaminetetraacetic acid (EDTA), nitrilotriacetic acid (NTA), diethylenetriaminepentaacetic acid (DTPA), 1,3-propylenediaminetetraacetic acid (1,3-PDTA), alaninediacetic acid (ADA), and methylglycinediacetic acid (MGD).

Multiple acid solutions having various combinations of a weak acid, a strong acid, and an aminopolycarboxylic acid are contemplated, such as by combining the various exemplary acids described above. The techniques described herein are generally applicable to solutions including at least a weak acid, a strong acid, and an aminopolycarboxylic acid to determine the concentrations of at least the weak acid and strong acid by titrating.

Figure 2:
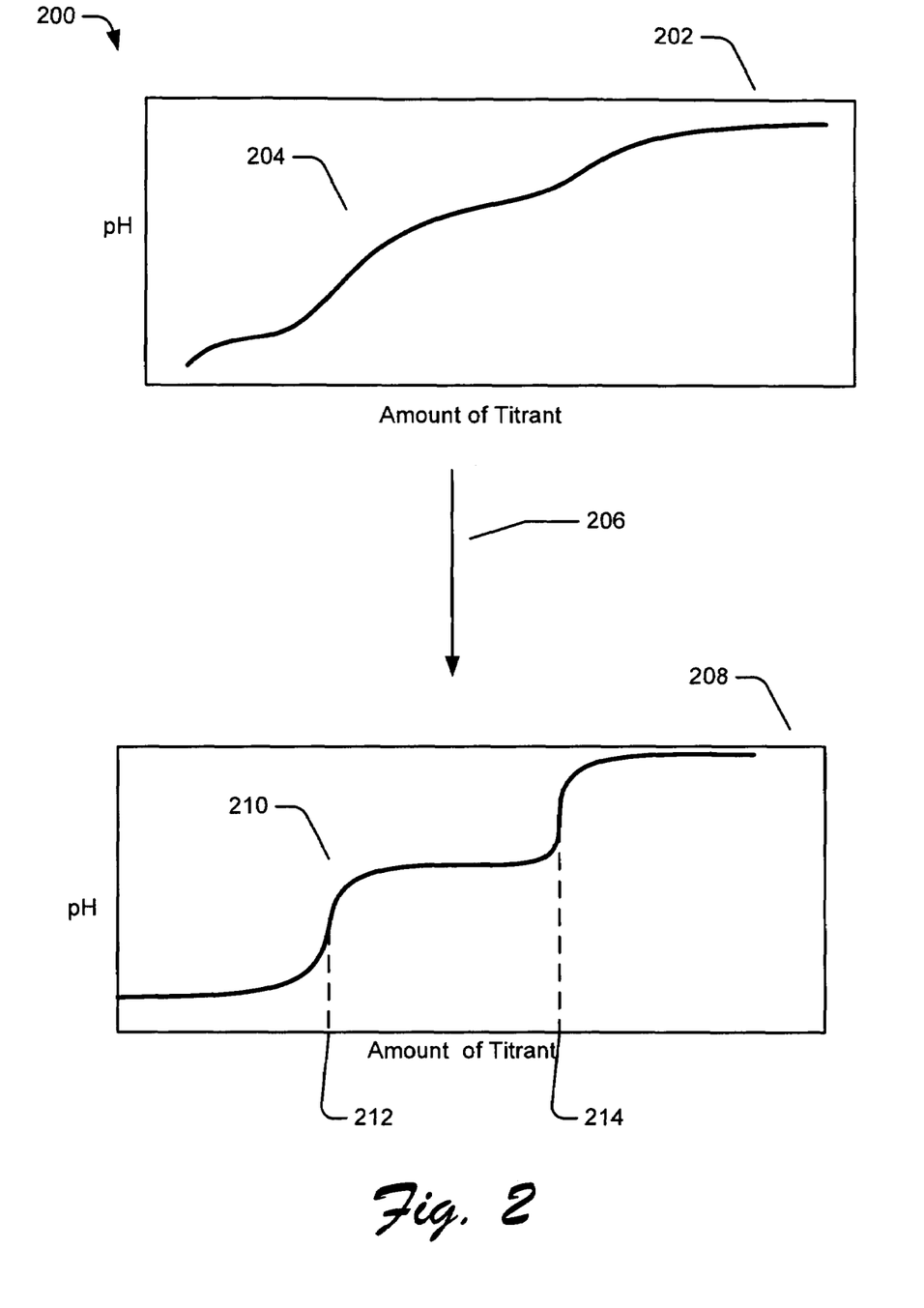
FIG. 2 depicts a representative illustration of the change in titration which may be observed with and without addition of metal halide to test samples of a multiple acid solution.

FIG. 2 depicts a representative illustration 200 which represents the change in titration which may be observed with and without addition of metal halide to test samples of a multiple acid solution. FIG. 2 is meant to illustrate characteristics of titrations performed with and without the addition of metal halides, and not necessarily actual outputs. For instance, an automatic titration device may be configured to analyze titration data without outputting the titration curves as in FIG. 2.

The upper portion of FIG. 2 depicts a representative chart 202 of a titration performed on a sample of solution without or prior to the addition of a metal halide. The plot 202 illustrates a titration curve 204 which shows the results of the titration. In particular, titration curve 204 shows the change in the pH of the sample versus the amount of titrant added (typically the volume added). The solution contains a weak acid, a strong acid, and an aminopolycarboxylic acid which for the purposes of example may be acetic acid, hydrochloric acid and EDTA respectively. In this example, the EDTA interferes with the titration such that endpoints corresponding to the various components are not discernable. In other words, the carboxyl groups of EDTA will prevent accurate determination of the endpoints. When this interference is present, the endpoints for the titration may not appear at all, may be fuzzy rather than sharp, or otherwise may be hard to determine. For instance, titration curve 204 depicted in FIG. 2 does not have sharp or readily determinable endpoints. Accordingly, determining the concentrations of acetic acid and hydrochloric acid in the sample may be difficult and even impossible via titration.

The arrow 206 represents addition of a metal halide to a sample in sufficient amounts to reduce and/or substantially remove the interference effects of aminopolycarboxylic acid during the titration. In particular, in this example a complex between the metal halide and the EDTA is formed, such that the effects of EDTA on the titration are substantially removed.

Following addition of a metal halide in sufficient amounts, a titration may be used to determine the concentration of the strong and weak acids of the sample. The lower portion of FIG. 2 depicts a representative chart 208 of a titration performed on a sample of solution following addition of a metal halide. In this case, the resultant titration curve 210 (also showing pH versus amount of titrant) is readily interpreted with sharp endpoints. Those skilled in the art will appreciate that discernable endpoints 212 and 214 are depicted. The endpoints 212 and 214 correspond to the amount of the basic titrant (e.g., NaOH or other base) added to consume the acids in solution. In the depiction of FIG. 2, the first endpoint 212 corresponds to the strong acid (HCL) and the second endpoint 214 corresponds to the weak acid (acetic acid) and may be used to calculate the respective concentrations. For instance, concentrations may be calculated via titration calculations as follows:

$$Cs*Vs=Ct*E1 \text{ or } Cs=(Ct*E1)/Vs \text{ and};$$

$$Cw*Vs=Ct*E2\text{-}E1 \text{ or } Cw=(Ct*(E2\text{-}E1))/Vs$$

where:
Cs=concentration of the strong acid
Cw=concentration of the weak acid
Vs=volume of the sample (e.g., the tested multiple acid solution)
Ct=concentration of the titrant
E1=the amount of titrant added at first endpoint
E2=the amount of titrant added at the second endpoint It is noted, that the amount of metal halide added to remove or nearly remove the effect of an aminopolycarboxylic acid may be used to determine the amount/concentration of the aminopolycarboxylic acid in solution. For instance, the formed complex may be a stable one to one complex between the metal halide and aminopolycarboxylic acid in the solution. In another case, the complex may be formed in a different ratio, such as one to two and so forth. Knowing the amount of metal halide added and the ratio, the corresponding amount of aminopolycarboxylic acid may be determined.

Naturally, the amount of metal halide which may substantially remove the adverse effects on the titration of a solution will depend on the amount of aminopolycarboxylic acid in the solution. A variety of techniques may be employed to determine when a sufficient amount of metal halide has been added. In an implementation, the amount of metal halide sufficient to substantially remove effects of an aminopolycarboxylic acid may be determined by trial and error. For instance, a series of samples with varying amounts of metal halide added may each be titrated. Thus, a variety of curves which fall somewhere between those depicted in charts 202 and 208 may be obtained. As the amount of metal halide sufficient to complex most of the aminopolycarboxylic acid in the solution is approached, the resulting titration curves will change from a relatively poor or undefined curve such as curve 204, to a curve having more clearly defined endpoints, such as the curve 210. When, successive changes to the curves sufficiently diminish, this may indicate that the aminopolycarboxylic acid has been sufficiently complexed to substantially remove the associated interference. That is, the baseline in plot 202 (without addition of metal halide) may be compared to curves produced with varying amounts of metal halide until a defined curve with sharp endpoints such as in plot 208 is approached. Thus, FIG. 2 also illustrates the change in the characteristics of titration performed on successive samples, which may be used to determine the amount of metal halide sufficient to "tie-up" most of the aminopolycarboxylic acid in the solution.

It is contemplated that a variety of other techniques may also be employed to determine when a sufficient amount of metal halide has been added such as spectroscopy, optical analysis, nuclear magnetic resonance, and other suitable analytical techniques to detect when the aminopolycarboxylic acid has been "tied-up" in a complex with the metal halide.

In one or more embodiments, the metal halide is formed from one of the transition metals in group 10 of the periodic table of elements, which consists of the transition metals nickel (Ni), palladium (Pd), platinum (Pt), and darmstadtium (Ds). These group 10 transition metals may be combined to form compounds with the halogens (Chlorine, Fluorine, Bromine, Iodine) which include but are not limited to Palladium (II) chloride, Platinum hexafluoride, Platinum(II) chloride, Platinum(IV) chloride, Nickel(II) chloride and so forth. These halide compounds of group 10 transition metals have been found to be suitable for forming stable complexes with aminopolycarboxylic acids in a multiple acid solution.

Figure 3:
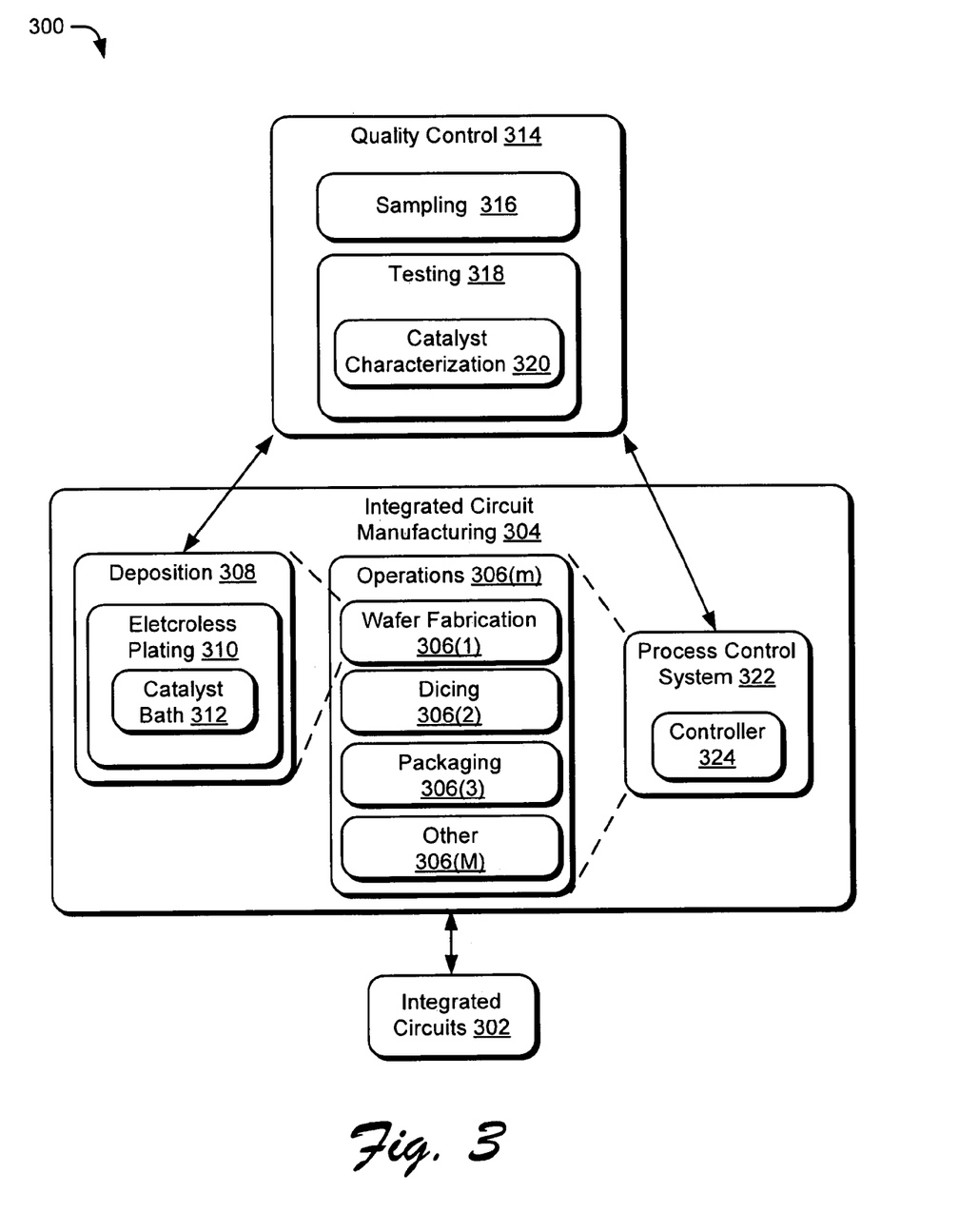
FIG. 3 depicts an exemplary implementation of an environment suitable for the manufacture of integrated circuits and which may employ described techniques for determining the component concentrations of a multiple acid solution.

FIG. 3 illustrates an exemplary implementation depicting an environment 300 suitable for the manufacture of integrated circuits 302. The environment 300 is described to provide a tangible example, of a process in which multiple acid solutions and techniques described herein for characterizing the multiple acid solutions may be employed and is not intended to limit the techniques to the manufacture of integrated circuits. A variety of processes and operations are contemplated in which multiple acid solution characterization techniques may be employed.

A plurality of integrated circuit 302 may be produced in an integrated circuit manufacturing process 304 which includes a variety of operations 306(m) (where "m" may be any number from one to "M"). For instance, FIG. 3 depicts a number of representative operations 306(m) including a wafer fabrication 306(1) operation in which semiconductive wafers having associated circuitry and electronic devices (e.g., transistors, vias, trenches, wiring, interconnects, gates and so on) may be fabricated. Those skilled in the art will appreciate that a variety of techniques may be used to produce semiconductive wafers with associated circuitry and/or electronic devices. The semiconductive material used for the wafers may comprise any material suitable for forming an integrated circuit 302, such as mono-crystalline silicon or other suitable semiconductors.

Also depicted is a dicing operation 306(2) in which a fabricated wafer may be divided into individual portion or "dice" for production of individual integrated circuits 302. Further, a packaging 306(3) operation may occur in which "dice" are joined or bonded to a package such as a printed circuit board (PCB) to form a plurality of integrated circuits. A variety of other 306(M) operations may be involved at various stages in the production of integrated circuits 302 including but not limited to semiconductor preparation, etching, masking, deposition, polishing, doping, ion implantation, trenching, lithography and so forth.

In an implementation, wafer fabrication 306(2) includes one or more deposition 308 operations. Generally, deposition refers to processes that deposit, form, coat, or otherwise transfer a material onto a semiconductive wafer. More particularly, a selected material may be deposited upon a semiconductive wafer to form structures, thin films, electronic devices, wiring, interconnections and so forth. Deposition may encompass a variety of processes such as chemical vapor deposition (CVD), electrochemical deposition (ECD), plating and so forth. A variety of deposition techniques are typically used in the manufacture of integrated circuits 302 and a plurality of deposition 308 operations may be involved in production of one integrated circuit 302, as those skilled in the art will appreciate.

For instance, FIG. 3 further depicts an electroless plating 310 operation which may be one of many deposition 308 operations performed in production of integrated circuits 302. More particularly, the surface of a semiconductive wafer or portions thereof may be plated with copper. The plating for instance may be performed to fill trenches and vias formed in semiconductive wafer with conductive material, to produce a thin material layer, to produce "on chip" wiring, and so forth. In an implementation, the electroless plating operation 310 may be configured to plate a semiconductive wafer or other substrate with copper. A variety of other materials may also be plated via electroless plating 310 operations including but not limited to gold, nickel, platinum and so forth. In an implementation, electroless plating 310 includes a catalyst bath 312 which is configured to prepare the semiconductive wafer for the plating with a material such as copper, gold and so forth. The semiconductive wafer may be dipped into the bath to produce activated sites (e.g., catalyzed sites) to which a selected material may be plated.

The catalyst bath 312 may be a multiple acid solution which may be characterized in accordance with the techniques described herein. In other words, the bath includes a weak acid, a strong acid, and an aminopolycarboxylic acid. In an embodiment a solution including hydrochloric acid, acetic acid and ethylenediaminetetraacetic (EDTA) may be used for a catalyst bath 310 in electroless plating of copper. For instance, the catalyst bath 312 catalyzes the reduction of copper introduced as cupric ions (copper II) to elemental copper in the electroless plating 310 operation. Further, the EDTA in the catalyst bath 312 may act as a complexing agent which assists in the adherence of the copper to the surface of the semi-conductive wafer. In other embodiments, other aminopolycarboxylic acids may act as complexing agents for other desired plating materials.

FIG. 3 further includes quality control 314 operation associated with integrated circuit manufacturing 304. Quality control 314 operation represents processes, devices, techniques, logic, and functionality for monitoring the quality of integrated circuits 302, integrated circuit manufacturing 304, operations 306(m), and so forth. For instance, quality control 314 is depicted as including sampling 316 and testing 318 operations which may be performed by technicians, devices and combinations thereof. Thus, the quality control 314 may obtain or receive samples which may be tested, such as to determine if the samples meet defined specifications, quality requirements, qualification parameters, customer requirements, desired process conditions and so forth. In an implementation, testing 318 may include catalyst characterization 320 in which techniques for determining the concentrations of a solution having multiple acids may be performed. In particular, techniques as previously described in reference to FIG. 1 and FIG. 2 may be used to determine the concentrations in a solution configured for the catalyst bath 312.

The results of quality control sampling 316 and 318 testing may then be used to make responsive actions, decisions, process adjustments and so forth. For instance, quality of incoming batches of solution for catalyst bath 312 may be sampled and tested. When the composition of the solution is not acceptable, the batch may be rejected or adjusted. Additionally, the catalyst bath 312 may be tested while it is being used in the electroless plating 310 operation to determine when it may need to be replaced, dumped, adjusted, and so forth. In other environments, the testing results of a variety of multiple acid solutions may form the basis for a variety of decisions, process adjustments and so forth. Further discussion of taking responsive actions based upon results obtained from application of multiple acid solution characterization techniques to a solution may be found in relation to FIG. 4.

A process control system 322 is illustrated which includes a variety of automatic controls, logic and so forth which may be employed to facilitate actions taken in response to testing 318, as well as for the performance of operations 306(m).

Process control system 322 represents functionality and devices operable to make process and operational changes within the environment 300. For instance, process control system 322 may include one or more controllers 324 which represent functionality and logic to receive inputs from the process and/or technicians including results of testing 318, to analyze the inputs, to command process changes, and so forth.

Figure 4:
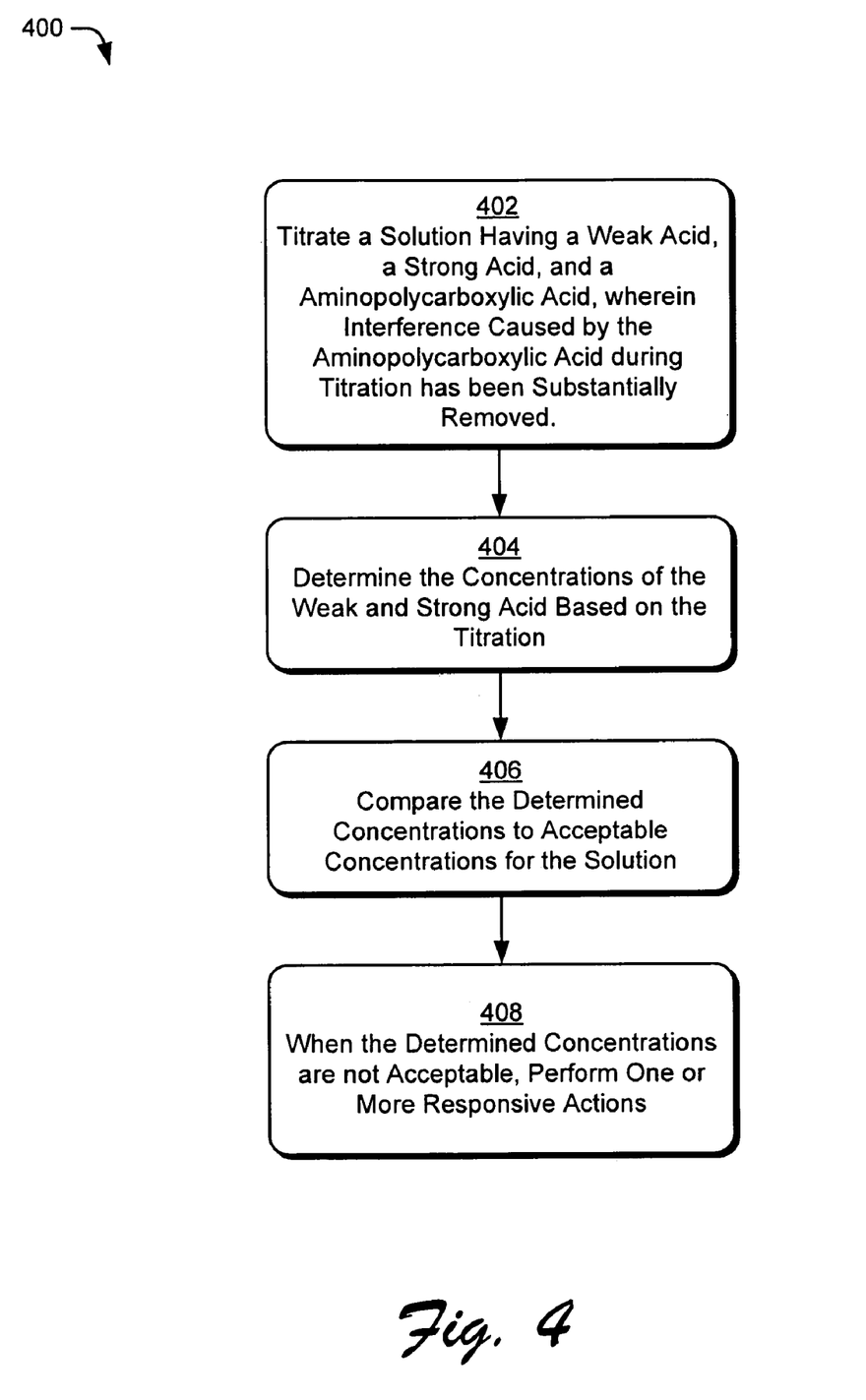
FIG. 4 depicts a flow diagram of an exemplary procedure in which one or more responsive actions are made based upon a titration of a multiple acid solution.

FIG. 4 depicts a flow diagram of an exemplary procedure 400 in which a responsive actions are made based upon a titration of a multiple acid solution. In the discussion of FIG. 4 reference will also be made to the environment of FIG. 3.

A titration is performed for a solution having a weak acid, a strong acid, and an aminopolycarboxylic acid, wherein interference caused by the aminopolycarboxylic acid during titration has been substantially minimized (block 402). For example the solution may be a solution configured to be used within the environment 300, such as for the catalyst bath 312. One suitable solution for a catalyst bath 312 includes hydrochloric acid, acetic acid and EDTA. A sample may be obtained from the catalyst bath 312 in operation, from a stock solution to be used in the catalyst bath, from a supplier, and so forth. The sample may be tested, such as by quality control 314 operation which may include catalyst characterization 320 in which a titration is performed to determine concentrations of one or more of the acids in the solution. In accordance with the techniques described, an amount of metal halide, and in particular a halide compound of a group 10 transition metal, may be added to a test sample of solution (e.g., a test solution) in an amount sufficient to substantially reduce interference of the aminopolycarboxylic acid during the titration. For instance, nickel chloride may be added to the solution to form an approximately one to one complex with the EDTA, such that the EDTA will not interfere with the subsequent titration.

The concentrations of the weak and strong acid are determined based on the titration (block 404) and the determined concentrations are compared to acceptable concentrations for the solution (block 406). For example, the titration may produce data such as endpoints previously described which may be used to calculate concentrations of the hydrochloric acid and acetic acid in the present example of a catalyst bath 312 solution. Specified control limits (e.g. upper and/or lower limits) may be specified for the catalyst bath 312 solution and components of the solution, such that process variation in the integrated circuit manufacturing 304 may be reduced, to ensure quality of supplied solution, to meet product or customer specifications, to produce a desired plating result (e.g., a particular plating thickness) and so forth. The determined concentrations may then be compared to respective control limits to determine if they fall within an acceptable concentration range, e.g., with the specified limits.

When the determined concentrations are not acceptable one or more responsive actions are performed (block 408). A variety of responsive actions to correct the concentrations and/or products produced with unacceptable concentrations are contemplated including but not limited to discarding and replacing the solution; identifying, quarantining and/or discarding associated products; retesting, adjusting or modifying the concentration of the solution; dumping a batch of the solution; and so on. Thus, results of the titration may trigger a variety of corrective actions. These actions may be performed by a technician, by automatic process controls, and combinations thereof. For example, in the previous example of a catalyst bath 312 solutions, if based on the titration the concentrations of an incoming batch of solution fall outside an acceptable range, the solution may be identified and not used in the manufacturing process, e.g., environment 300. In another example, a catalyst bath 312 solution which is already being used in the process may be discarded, modified and so forth when the results of a titration show concentrations outside of acceptable limits. Further, products (e.g. integrated circuits 302) produced with a "bad" solution may be identified, quarantined, discarded, reprocessed, and so forth. In this manner the multiple acid solution characterization techniques described herein may be employed to take actions which may result in improved quality and consistency of a solution and/or associated operations, manufacturing processes, products, results and so forth.

While multiple acid solutions used for catalyst bath 312 have been described, it is again noted that solutions including a weak acid, a strong acid, and an aminopolycarboxylic acid may be used for a variety of purposes throughout the environment 300 as well as in other environments. The described techniques are generally applicable to solutions which include a weak acid, a strong acid, and an aminopolycarboxylic acid to determine by titration the concentrations of the weak and strong acids without interference from the aminopolycarboxylic acid.

CONCLUSION

Although the invention has been described in language specific to structural features and/or methodological acts, it is to be understood that the invention defined in the appended claims is not necessarily limited to the specific features or acts described. Rather, the specific features and acts are disclosed as exemplary forms of implementing the claimed invention.

What is claimed is:

1. A method comprising:
   adding a sufficient amount of one or more metal halide compounds of transition metals from group 10 to a solution that contains an aminopolycarboxylic acid, a weak acid and a strong acid to substantially reduce interference caused by the aminopolycarboxylic acid during titration; and
   titrating the solution to determine concentrations of the weak acid and the strong acid in the solution.

2. A method as recited in claim 1, wherein the one or more metal halide when added to the solution forms a complex with the carboxyl groups of the aminopolycarboxylic acid which removes interference during titration.

3. A method as recited in claim 1, wherein the interference comprises hindering the establishment of identifiable endpoints by titration.

4. A method as recited in claim 1, wherein the titration establishes endpoints corresponding to the weak and strong acid which correspond to the concentrations of the weak acid and strong acid in the solution.

5. A method as recited in claim 1, wherein the weak acid is selected from the group consisting of:
   acetic acid;
   citric acid;
   boric acid; and
   formic acid.

6. A method as recited in claim 1, wherein the strong acid is selected from the group consisting of:
   hydrochloric acid;
   hydrobromic acid;
   hydroiodic acid;
   sulfuric acid;
   nitric acid;
   perchioric acid; and
   chioric acid.

7. A method as recited in claim 1, wherein the arninopolycarboxylic acid is selected from the group consisting of:
ethylenediaminetetraacetic (EDTA);
nitrilotriacetic acid (NTA);
diethylenetriaminepentaacetic (DTPA);
1,3-propylenediaminetetraacetic acid (1,3-PDTA);
alaninediacetic acid (ADA); and
methyiglycinediacetic acid (MGD).

8. A method as recited in claim 1, wherein the solution is used in one or more operations to produce a plurality of integrated circuits.

9. A method as recited in claim 1, wherein the solution is used in as a catalyst bath in an electroless plating operation.

10. A method as recited in claim 9, wherein the electroless plating operation comprises plating of copper on a semiconductive wafer.

11. A method as recited in claim 1, wherein the amount of metal halide sufficient to substantially remove interference with the titration is determined by successively titrating samples with different amounts of metal halide added until a titration with identifiable endpoints is established.

12. A method as recited in claim 1, wherein the amount of metal halide sufficient to substantially remove interference with the titration is determined by spectroscopy.

13. A method comprising:
obtaining a sample of a solution including:
a weak acid;
a strong acid; and
an aminopolycarboxylic acid;
determining the concentrations of the weak acid and the strong acid in the solution via a titration; wherein
the aminopolycarboxylic acid causes interference with titration of the solution which prevents determination of the concentrations; and
the interference is substantially removed by addition of one or more metal halide compounds of transition metals from group 10 to the solution.

14. A method as recited in claim 13, wherein the weak acid is acetic acid, the strong acid is hydrochloric acid and the aminopolycarboxylic acid is ethylenediaminetetraacetic (EDTA).

15. A method as recited in claim 13, wherein the addition of the one or more metal halide results in formation of a complex between the metal halide and the aminopolycarboxylic acid which substantially removes the interference of the aminopolycarboxylic during titration.

16. A method as recited in claim 15, wherein a plurality of carboxyl groups of the aminopolycarboxylic are liganded to the added metal halide via the complex, such that the carboxyl groups do not interfere with the titration.

17. A method comprising:
sampling a batch of solution configured for use as a catalyst in electroless plating, the solution including:
a weak acid;
a strong acid; and
an aminopolycarboxylic acid;
adding to the sample at least one halide compound of a group ten metal to remove interference caused by the aminopolycarboxylic acid with titrafion of the sample; and
performing a titration of the sample to determine the concentration of one or more component of the batch of solution.

18. A method as recited in claim 17 further comprising;
determining whether the concentrations of one or more acid in the sample meets one or more control limits specified for the batch of solution; and
when one or more of the concentrations fails to meet respective control limits, perform one or more actions to correct the concentrations of the batch of solution.

19. A method as recited in claim 18, wherein the one or more actions include replacing the batch of solution used for the electroless plating.

20. A method as in claim 18, wherein the one or more actions include modifying the concentrations of the batch of solution to meet the one or more specified control limits.

21. A method as in claim 18, wherein the one or more actions include using automatic controls to correct the concentration of the batch of catalyst solution.

22. A method as in claim 17, wherein the electroless plating is performed on a semiconductive wafer to produce one or more integrated circuits.

23. A method as recited in claim 17, wherein the weak acid is acetic acid, the strong acid is hydrochloric acid and the aminopolycarboxylic acid is ethylenediaminetetraacetic (EDTA).

* * * * *

UNITED STATES PATENT AND TRADEMARK OFFICE
CERTIFICATE OF CORRECTION

PATENT NO. : 7,622,305 B2  Page 1 of 1
APPLICATION NO. : 11/509981
DATED : November 24, 2009
INVENTOR(S) : Choi et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 533 days.

Signed and Sealed this

Twenty-sixth Day of October, 2010

David J. Kappos
*Director of the United States Patent and Trademark Office*